(12) United States Patent
Amano et al.

(10) Patent No.: US 6,277,134 B1
(45) Date of Patent: *Aug. 21, 2001

(54) CORNEAL SURGICAL APPARATUS (75) Inventors: Masanori Amano, Aichi; Takashi Hagiwara, Saitama, both of (JP)

(73) Assignee: Nidek Co., Ltd., Aichi (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/126,595

(22) Filed: Jul. 31, 1998

(30) Foreign Application Priority Data

Jul. 31, 1997 (JP) .................................................... 9-220806
Jun. 5, 1998 (JP) ................................................... 10-157127

(51) Int. Cl.[7] ...................................................... A61F 9/00
(52) U.S. Cl. ............................................ 606/166; 606/167
(58) Field of Search ............................... 606/1, 107, 130, 606/159, 160, 167, 170, 171, 184, 185; 604/19, 22

(56) References Cited

U.S. PATENT DOCUMENTS

Re. 35,421   1/1997   Ruiz et al. .
4,662,370    5/1987   Hoffmann et al. .
4,903,695    2/1990   Warner et al. .
5,586,980   12/1996   Kremer et al. .
5,595,570    1/1997   Smith .
5,624,456    4/1997   Hellenkamp .
5,772,675 *  6/1998   Hellenkamp .......................... 606/166

FOREIGN PATENT DOCUMENTS

197803  * 3/1978  (DE) ..................................... 606/166
3433581 * 3/1986  (DE) ..................................... 606/166

* cited by examiner

Primary Examiner—Glenn K. Dawson
(74) Attorney, Agent, or Firm—Sughrue, Mion, Zinn, Macpeak & Seas, PLLC (57) ABSTRACT

A corneal surgical apparatus, which can smoothly incise the cornea (particularly the Bowman's membrane at the cutting start) while ensuring the cutting ability of the blade with a simple arrangement. After a suction unit is fixed to a periphery of the cornea of patient's eye, the cornea projecting from an opening portion provided in the suction unit is applanated substantially flatly, and the applanated cornea is incised in a layered form by a blade. The blade is moved such that any point on the blade depicts an arcuate locus of the same shape.

22 Claims, 6 Drawing Sheets

CORNEAL SURGICAL APPARATUS

BACKGROUND OF THE INVENTION

The present invention relates to a corneal surgical apparatus for incising the cornea of patient's eye in a layered form in keratorefractive surgery or photorefractive keratectomy (PRK).

In recent years, attention has been focused on LASIK (laser in situ keratomileusis) for effecting keratomileusis (keratorefractive) treatment wherein after a flap is formed by incising a corneal portion of 150 μm thickness ranging from the corneal epithelium to the corneal stroma with one end of the corneal portion remaining connected like a hinge, the corneal stroma is cut away or ablated in a refractive correction amount by Excimer laser light, and the flap is returned to its original position. In this surgery, a corneal surgical apparatus called microkeratome is used to incise the cornea in a layered form. So called "upper hinge flap method" in which the hinge is formed on the upper side (upper eyelid side) of the patient's eye is effective to prevent the deviation and the like of the flap during adhesion of the cornea after the surgery is complete, and thus generally adopted to the PRK recently.

A typical microkeratome includes a suction unit for vacuum-adhering a corneal surface, a cornea applanating member for applanating a corneal portion projecting from an opening portion of the suction unit, and a blade linearly moved in the direction toward the hinge while being oscillated in the lateral direction so as to incise the applanated corneal portion into a layered form with a substantially uniform thickness.

In addition, in recent years, there has been proposed a microkeratome having a blade which is pivoted by using a single pivotal axis as its reference while oscillating the blade so as to form a hinged flap.

Each of these microkeratomes are designed to make oscillation of the blade for incision of the relatively hard Bowman's membrane underlying the corneal epithelium (particularly for the start of the cutting), but is disadvantageous in that a complicated mechanism is required to make the linear motion of the blade (or pivoting motion of the blade with one axis as the reference) while oscillating the blade.

With the type in which the blade is advanced linearly, a feeding mechanism for linearly feeding the blade and a holding mechanism thereof occupy an area in the feeding direction, so that the patient's cheek hinders the formation of the upper hinge flap.

On the other hand, with the type in which the blade is pivoted by using one axis as the reference, since the feeding pitches of the blade differ between the side close to the pivoting axis and the side remote from it, the incision differs depending on the position on the edge of the blade, so that the incised surface tends to be nonuniform.

SUMMARY OF THE INVENTION

In view of the above-described problems, it is an object of the present invention to provide a corneal surgical apparatus which is capable of effecting smooth incision with a simple mechanism.

It is another object of the present invention to provide a corneal surgical apparatus which makes it possible to easily form an upper hinge flap.

It is still another object of the present invention to provide a corneal surgical apparatus which is capable of smoothly effecting the incision by the blade and of obtaining a satisfactory incised surface.

To attain the above-noted and other objects, the present invention is characterized by being provided with the following features:

(1) A corneal surgical apparatus for incising a cornea of patient's eye in a layered form, comprising:

fixing means, having an opening, for fixing a periphery of said cornea relative to said apparatus so that said cornea projects from said opening;

applanating means for applanating said cornea projecting from said opening;

a blade for incising said cornea applanated by said applanating means; and moving means for moving said blade so that points on said blade depict arcuate loci of the same shape.

(2) A corneal surgical apparatus according to (1), wherein said blade is moved by said moving means without making an oscillating motion.

(3) A corneal surgical apparatus according to (1), wherein said moving means includes:

first and second links, each rotatably coupled to said blade, said first and second links being parallel to each other and equal in length to each other, and rotating means for rotating rotational shafts of said first link and said second link in synchronism with each other.

(4) A corneal surgical apparatus according to (1), wherein said moving means includes:

first and second links, each rotatably coupled to said blade, said first and second links being parallel to each other and equal in length to each other, and rotating means for rotating rotational shafts of said first link and said second link in synchronism with each other, and wherein positions of the rotational shafts of said first and said second links, and a position of an edge of said blade coupled to said first and said second links are determined in relation to a position of a center of said opening and a size of said opening, so that said opening provided in said fixing means partially remains outside of a movable range of said blade moved by said moving means.

(5) A corneal surgical apparatus according to (1), further comprising:

restricting means for restricting movement of said blade to secure a hinge in the cornea incised by said blade.

(6) A corneal surgical apparatus according to (1), further comprising:

suspending means for suspending and supporting said moving means, said applanating means, and said blade with respect to said fixing means.

(7) A corneal surgical apparatus according to (1), wherein a direction of an edge of said blade is in parallel to a longitudinal direction of said fixing means.

(8) A corneal surgical apparatus according to (1), wherein said moving means and said blade are bilaterally symmetrical, and said apparatus further comprising:

attaching means for attaching said moving means and said blade in an inverted form with respect to said fixing means.

(9) A corneal surgical apparatus according to (1), further comprising:

driving means for driving said moving means; and controlling means for controlling said driving means to vary a moving speed of said blade during incision.

(10) A microkeratome for use in photorefractive keratectomy, comprising:

a suction unit having a vacuum ring;

a coupling unit mounted on said suction unit;

a transfer unit mounted on said coupling unit and having a parallel link mechanism; and a cutting unit including:
  a base;
  a cornea applanating portion fixedly provided on said base; and
  a blade fixedly provided on said base,
wherein said base of said cutting unit is supported to said transfer unit by said parallel link mechanism.

(11) A microkeratome according to (10), wherein a relative positional relationship between said cornea applanating portion and said blade is kept constant by said base.

(12) A microkeratome according to (10), wherein said blade is in non-contact with said cornea applanating portion.

(13) A microkeratome according to (10), wherein said parallel link mechanism moves said base so that any portions on said blade orbits along arcuate loci of the same shape.

(14) A microkeratome according to (10), wherein said base of said cutting unit is rotationally mounted about a stationary point via said parallel link mechanism.

(15) A microkeratome according to (14), wherein said stationary point corresponds to a center of an opening of said suction unit.

(16) A microkeratome for use in photorefractive keratectomy, comprising:

a suction unit having a vacuum ring;

a coupling unit mounted on said suction unit;

a cutting unit having a blade;

a transfer unit mounted on said coupling unit and having a parallel link mechanism, wherein said cutting unit is rotationally mounted about a stationary point via said parallel link mechanism.

(17) A microkeratome according to (16), wherein said stationary point corresponds to a center of an opening of said suction unit.

(18) A parallel link mechanism, adapted to a microkeratome, for moving a blade to incise a cornea of patient's eye, said mechanism comprising:

a base; and a pair of links rotationally arranged with respect to said base about rotational axes, respectively, each of said links being rotatably supporting said blade so that said links are kinematically connected to each other through said blade, wherein said blade orbits relative to said base about an axis other than said rotational axes via said links.

(19) A parallel link mechanism according to (18), wherein any portions on said blade orbits along arcuate loci of the same shape via said links.

(20) A parallel link mechanism according to (18), wherein said blade is kept in parallel via said link during orbiting motion of said blade.

The present disclosure relates to the subject matter contained in Japanese patent application Nos. Hei. 9-220806 (filed on Jul. 31, 1997) and Hei. 10-157127 (filed on Jun. 5, 1998), which are expressly incorporated herein by reference in their entireties.

DETAILED DESCRIPTION OF THE PREFERRED EMBODIMENT

Figure 1A:
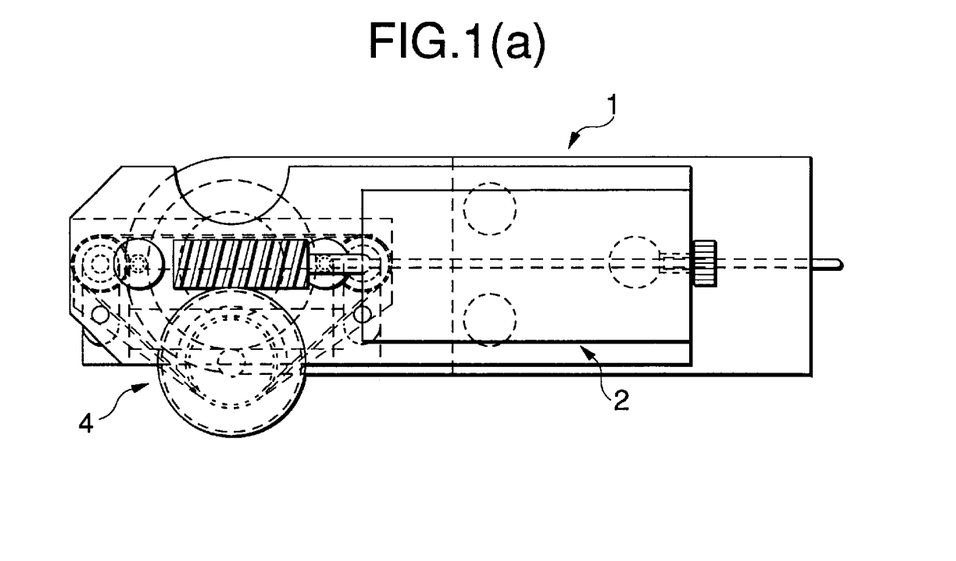
FIGS. 1(a) is a schematic top view of a corneal surgical apparatus in accordance with an embodiment.
Figure 1B:
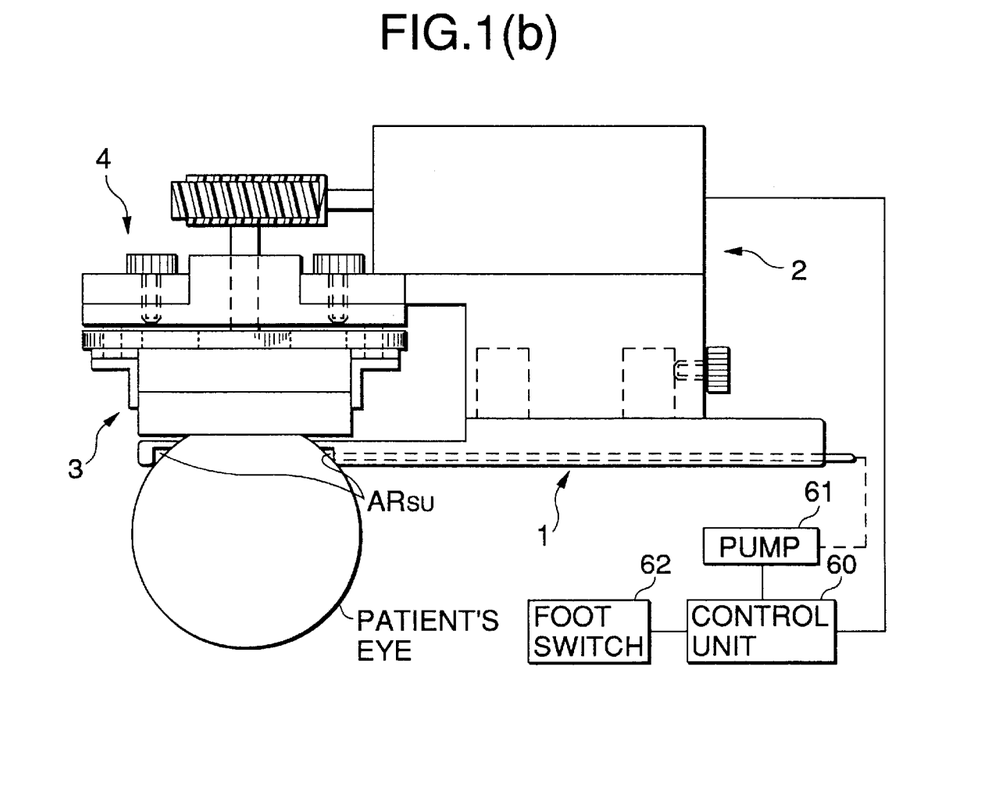
FIG. 1(b) is a schematic side elevational view thereof.

Referring to the drawings, a description will be given of an embodiment of the present invention. FIG. 1(a) is a top view of a corneal surgery apparatus body in accordance with the embodiment, and FIG. 1(b) is a side elevational view thereof and also illustrates the configuration of a control system. The corneal surgery apparatus body in accordance with this embodiment is largely classified into four units: a suction unit 1, a coupling unit 2, a cutting unit 3, and a transfer unit 4. It should be noted that FIGS. 1(a) and 1(b) show a state where patient's left eye is to be incised, and the apparatus body is disposed such that the upper side in FIG. 1(a) is set at the upper eyelid side of the patient's eye, and the right-hand side in FIG. 1(a) is set at the left ear side of the patient.

Figure 2A:
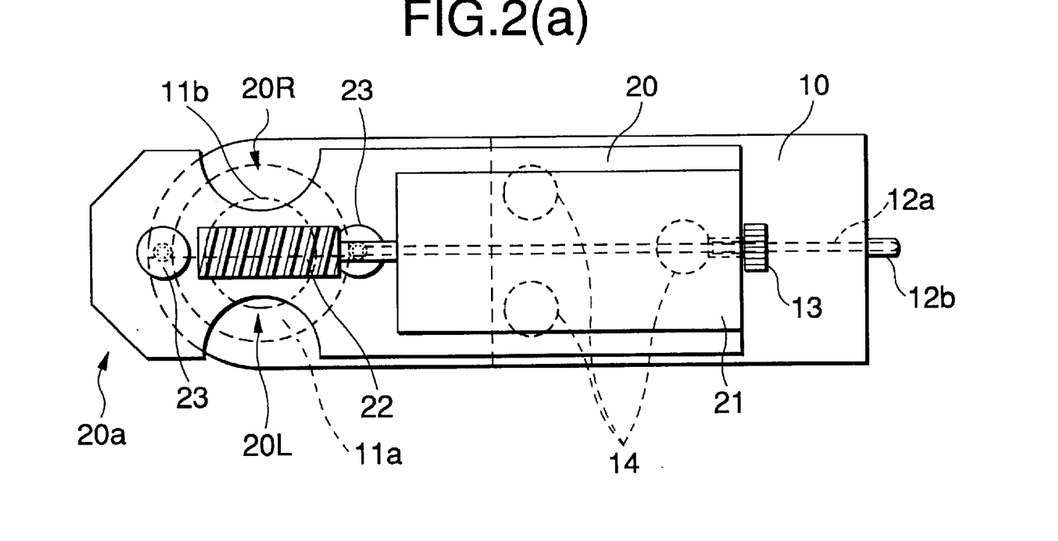
FIG. 2(a) is a schematic top view of a suction unit and a coupling unit.
Figure 2B:
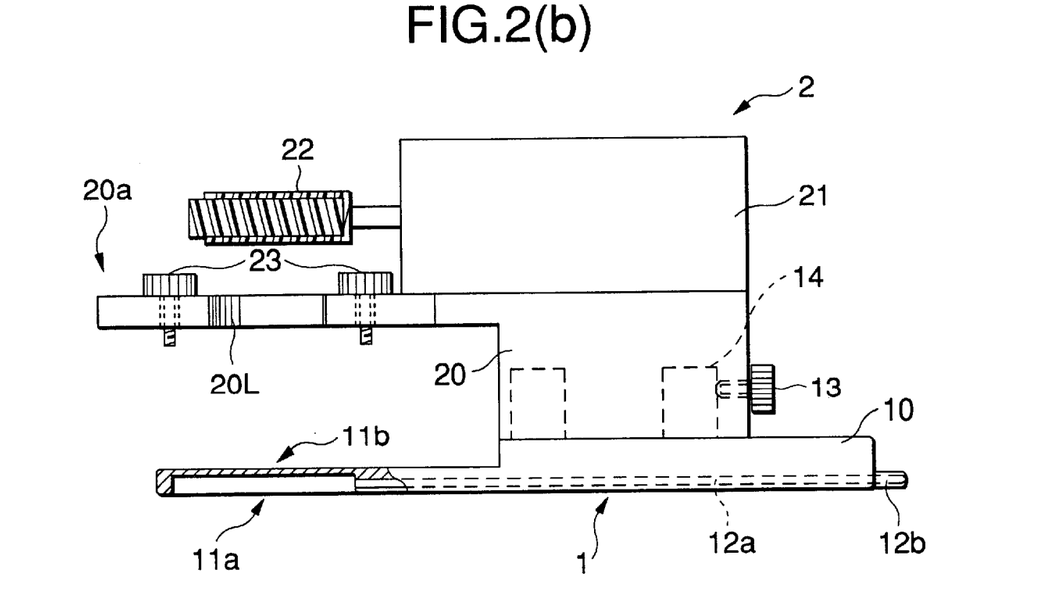
FIG. 2(b) is a schematic side elevational view thereof.
Figure 3A:
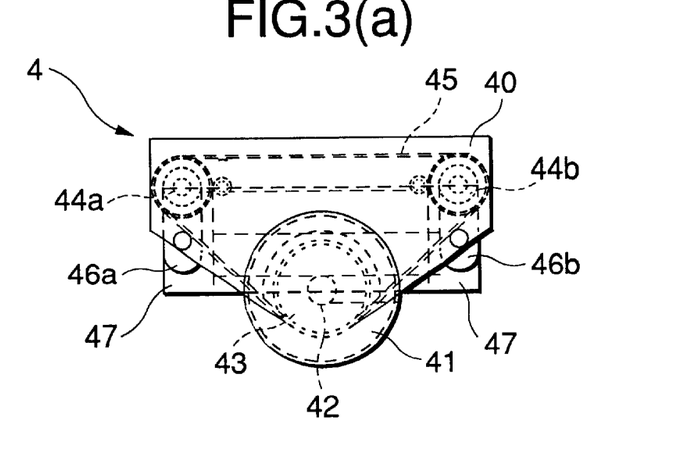
FIG. 3(a) is a schematic top view of a cutting unit and a transfer unit.
Figure 3B:
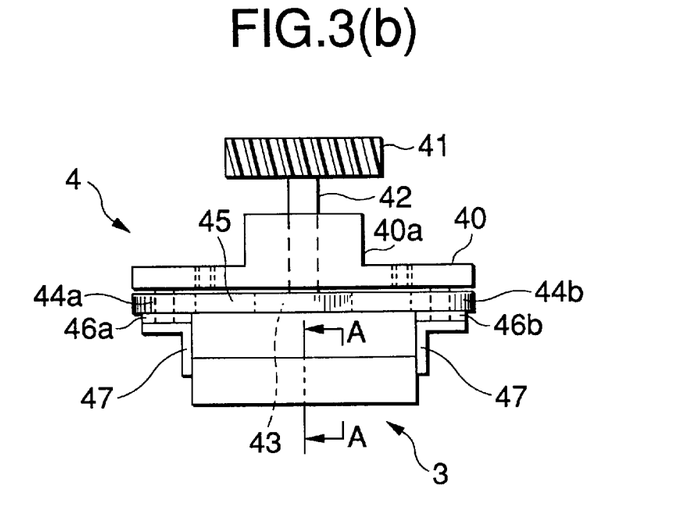
FIG. 3(b) is a schematic side elevational view thereof.
Figure 3C:
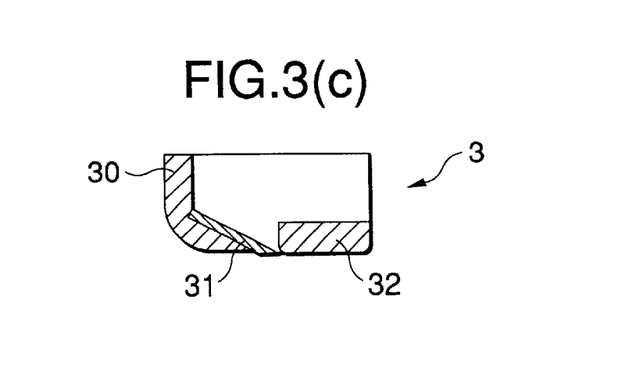
FIG. 3(c) is an enlarged sectional view taken along line A—A in FIG. 3(b)

Referring to FIGS. 2(a) to 3(c), a description will be given of the arrangements of the respective units. FIG. 2(a) is a top view of the state in which the coupling unit 2 is attached to the suction unit 1, and FIG. 2(b) is a side elevational view thereof (including a partly sectional view). FIG. 3(a) is a top view of the cutting unit 3 and the transfer unit 4, FIG. 3(b) is a side elevational view thereof, and FIG. 3(c) is an enlarged sectional view taken along line A—A in FIG. 3(b).

<Suction Unit>

As shown in FIGS. 2(a) and 2(b), a circular recessed portion 11a for contacting a sclera of the patient's eye and an opening portion 11b concentric with the recessed portion 11a are formed on the left-hand side of a suction base 10 provided in the suction unit 1. The recessed portion 11a is connected to a vacuum tube 12b via a suction passage 12a formed in the longitudinal direction of the suction base 10, the tube 12b extending to a vacuum pump 61. In surgery, a rim portion of the recessed portion 11a and a rim portion of the opening portion 11b are made in contact with the periphery of the cornea or with the conjunctiva, and the air in a gap $AR_{su}$ (see FIG. 1) which is secured by the contact is vacuum-discharged, thereby causing the suction base 10 to be vacuum-adhered and fixed to the patient's eye. In this fixation, as an operator holds the tube 12b side of the suction base 10, the positioning of the opening portion 11b can be facilitated, and the apparatus body can be held in a stable manner. In addition, three fixing guides 14 for mounting the coupling unit 2 are implanted on an upper portion of the suction base 10.

<Coupling Unit>

A coupling base 20 of the coupling unit 2 is provided with holes for insertion of the fixing guides 14 provided on the suction base 10, and the coupling unit 2 can be mounted and fixed to the suction base 10 by tightening a thumb screw member 13 against one of the fixing guides 14. A drive motor 21 is mounted on top of the coupling base 20, and a worm gear 22 is attached to a rotating shaft of the drive motor 21. This worm gear 22 is rotatively driven by the drive motor 21, which in turn drives the cutting unit 3 via the transfer unit 4 (which will be described later).

Two thumb screw members 23 for suspending and fixing the transfer unit 4 are provided on an arm 20a which is formed integrally with the coupling base 20. Further, notched portions 20L and 20R for avoiding interference with a base portion 40a provided in a base 40 of the transfer unit 4 are respectively formed in opposite side portions of the arm 20a. The transfer unit 4 can be selectively fixed with the base portion 40a disposed on the notched portion 20L for formation of an upper hinge flap of the patient's left eye, or with the base portion 40a disposed on the notched portion 20R for formation of an upper hinge flap of the patient's right eye.

<Cutting Unit>

The cutting unit 3 includes a blade 31 attached to a cutting base 30, and a cornea applanating portion 32. For the blade 31 itself, it is possible to use a mineral blade in which a mineral such as diamond, sapphire, or the like is used as its edge, or a metal blade in which stainless steel, steel, or the like is used as its edge.

<Transfer Unit>

The transfer unit 4 includes the transfer base 40 having the base portion 40a; a shaft 42 held rotatably on the base portion 40a; a worm wheel gear 41 fixed to a upper end of the shaft 42; a gear 43 fixed to a lower end of the shaft 42; two gears 44a and 44b rotatably supported on the lower side of the transfer base 40; a belt 45 suspended on the gears 43, 44a and 44b; two links 46a and 46b fixed to the respective gears 44a and 44b and arranged in parallel to each other; and two fixing members 47 rotatably supported at the other ends of the respective links 46a and 46b. The cutting unit 3 is screwed and fixed to the fixing members 47. A parallel crank mechanism is formed by the transfer base 40, the links 46a and 46b, the cutting unit 3, and the like.

The transfer base 40 is provided with threaded holes, through which the transfer base 40 is suspended from and fixed to the coupling unit 2 by the aforementioned screw members 23. This fixation causes the worm wheel gear 41 to mesh with the worm gear 22, so that the rotational torque of the drive motor 21 is transmitted to the gear 43 to rotate the gears 44a and 44b in synchronism with each other through the belt 45. In conjunction with this rotation, the links 46a and 46b are rotated about rotational centers of the gears 44a and 44b, respectively, thereby moving the blade 31 attached to the cutting unit 3 such that the direction of its blade maintains a fixed relation with respect to the apparatus (in a parallel relation to the longitudinal direction of the apparatus).

Figure 4:
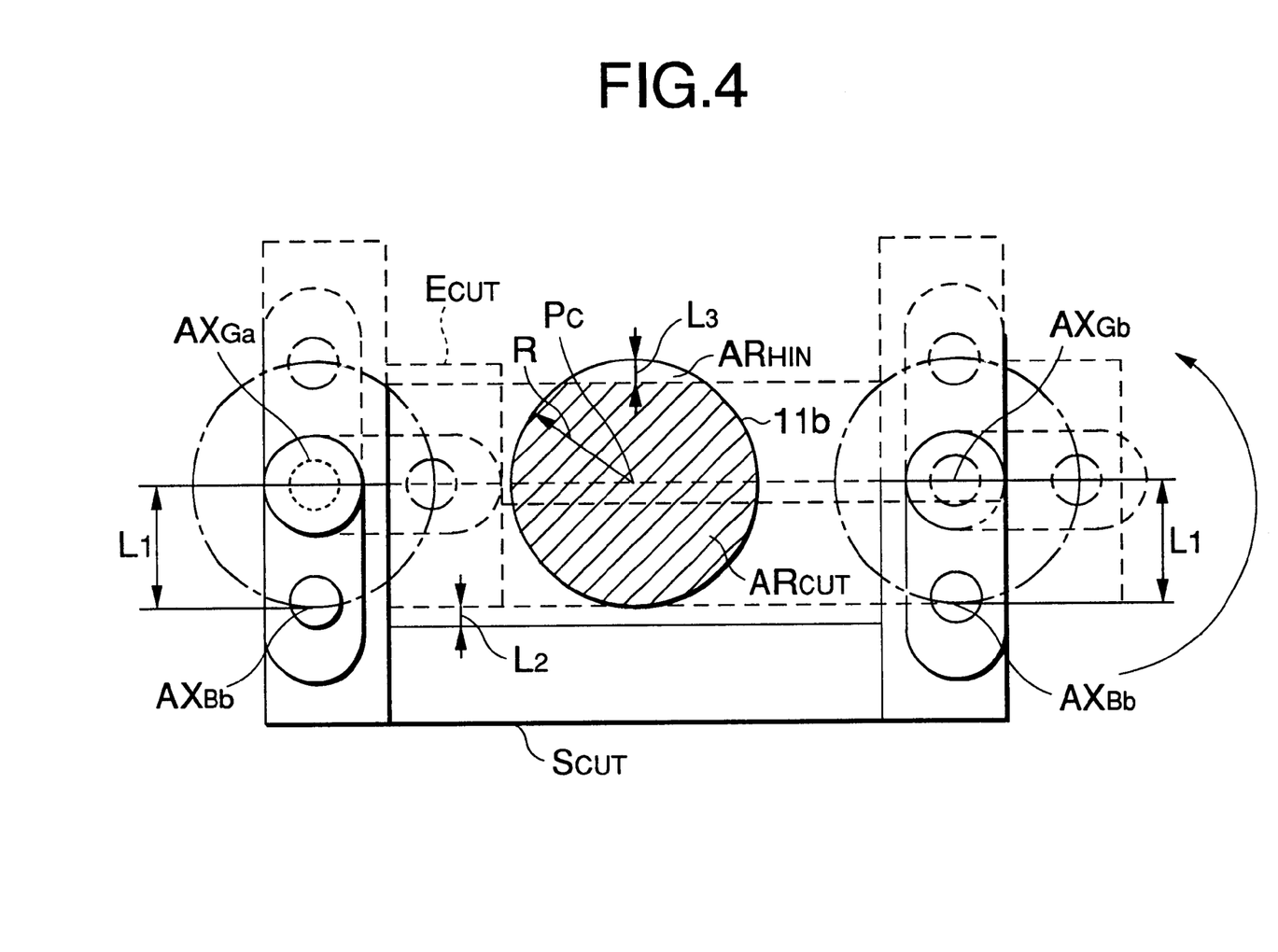
FIG. 4 is an explanatory diagram concerning the movement of a blade.

This embodiment is arranged such that the incision of the cornea is complete as the links 46a and 46b undergo one rotation around the rotational centers $AX_{Ga}$ and $AX_{Gb}$ as shown in FIG. 4. To ensure that the blade 31 rotatively moves with a hinge portion ($AR_{HIN}$) remaining in the cornea, the positions of the rotational centers $AX_{Ga}$ and $AX_{Gb}$ of the links 46a and 46b, the distance $L_1$ (link length) from the rotational centers $AX_{Ga}$ and $AX_{Gb}$ to the rotational centers $AX_{Ba}$ and $AX_{Bb}$ of the fixing members 47, and the distance $L_2$ from the rotational centers $AX_{Ba}$ and $AX_{Bb}$ to the edge of the blade 31 (when the straight line connecting $AX_{Ga}$ and $AX_{Ba}$ and the edge of the blade 31 become orthogonal) are determined in relation to the size of the opening portion 11b and its center PC. For example, if the rotational centers $AX_{Ga}$ and $AX_{Gb}$ and the opening center PC of the opening portion 11b are all aligned on the same straight line, and if the distance $L_1$ is set equal to the radius R of the opening portion 11b, the distance $L_2$ corresponds to the distance $L_3$ for securing the hinge portion $AR_{HIN}$.

In addition, the transfer unit 4 is bilaterally symmetrical, and the base portion 40a with the cutting unit 3 attached thereto can be selectively attached to one of the notched portions 20L and 20R of the coupling unit 2, to cope with surgery on the left and right eyes.

Operation of the apparatus thus constructed will be described hereafter. The following description is directed to a case where patient's left eye is to be subjected to operation. The coupling unit 2, the cutting unit 3, and the transfer unit 4 are preliminary attached in a manner as shown in FIGS. 1(a) and 1(b). The blade 31 of the cutting unit 3 is disposed at the initial position $S_{CUT}$ indicated by the solid lines in FIG. 4.

While confirming the state of inclination of the suction base 10 (apparatus body), the position of the pupillary center, and the like on the basis of a mark preliminary applied onto the patient's cornea with an instrument such as a marker, the operator installs the apparatus body such that the central portion of the opening portion 11b is located at the pupillary center of the patient's eye. In this installation of the apparatus body with respect to the patient's eye, the apparatus body is held with the tube 12b of the suction base 10 located on the left ear side of the patient.

After the installation of the suction base 10, the operator, while maintaining the installed position and posture of the suction base 10, drives the pump 61 to suck the air in the gap $AR_{SU}$ between the suction base 10 and the corneal surface to decrease the pressure therein. When the pressure in the gap $AR_{Su}$ is decreased to a predetermined level, the pump 61 is controlled by a control unit 60 so as to maintain that pressure. As a result, the suction base 10 is vacuum-adhered and fixed to the patient's eye.

Figure 5A:
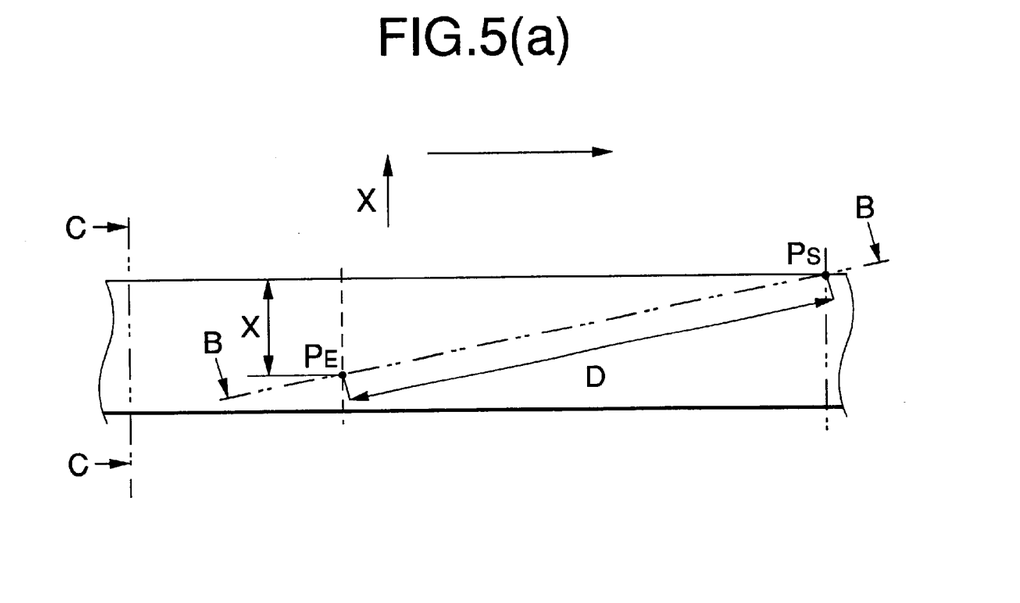
FIG. 5(a) is an explanatory diagram concerning the cutting angle.
Figure 5B:
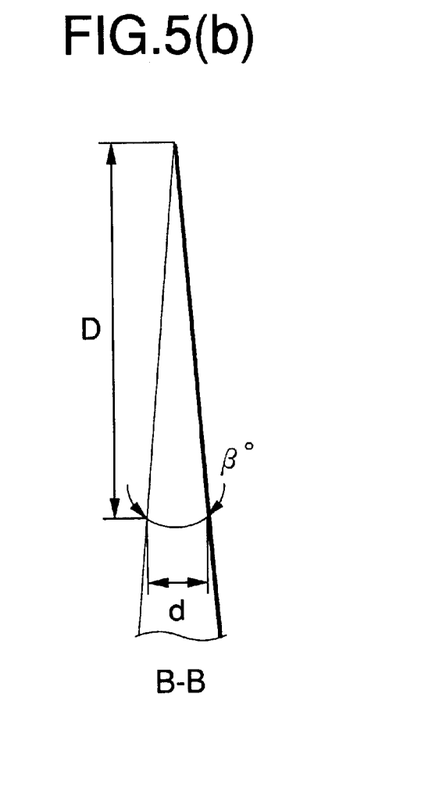
FIG. 5(b) is a sectional view taken along line B—B in FIG. 5(a)
Figure 5C:
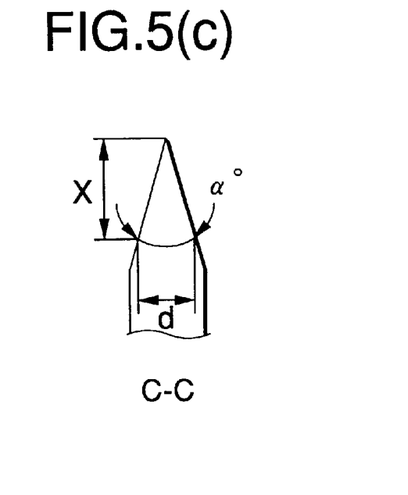
FIG. 5(c) is a sectional view taken along line C—C in FIG. 5(a); and Each of FIGS. 6(a) and 6(b) is an explanatory diagram concerning a blade moving link mechanism in accordance with a modification.

After completion of the fixation of the apparatus, the operator operates a foot switch 62 to rotate the drive motor 21, thereby rotatively moving the cutting unit 3. The edge of the blade 31 contacts the cornea while its direction is kept to a fixed direction by the parallel crank mechanism. At the start of cutting the cornea, since the blade 31 moves while sliding in the lateral direction, the blade 31 is able to cut through while smoothly incising even the relatively hard Bowman's membrane underlying the corneal epithelium. The reason for this will be explained with reference to the explanatory diagram on the cutting angle shown in FIGS. 5(a) to 5(c). If the blade is moved the distance x to the upper side while sliding in the rightward direction in FIG. 5(a), the point of the object to be cut, which contacts the edge of the blade at a point $P_S$, relatively moves along a locus $P_S-P_E$ on the blade, and its moving distance is D. If the thickness of the blade at a point distanced x from its edge is assumed to be d, a cutting angle β during this cutting can be considered as an angle formed by a cross-sectional shape of the edge of the blade taken along the locus $P_S-P_E$ (B—B section), and the cutting angle β is sharper than a cutting angle α possessed by the blade (C—C section). In other words, the same effect can be obtained as a case where cutting is effected by linearly advancing a blade having an edge configuration with the cutting angle β. Therefore, it is possible to incise the hard Bowman's membrane relatively easily.

As shown in FIG. 4, the blade 31 moves to a position $E_{CUT}$ (dotted line) by the 180° rotation of the links 46a and 46b using the parallel crank mechanism to incise the cornea, which is applanated by the cornea applanating portion 32, with a substantially uniform thickness in an area $AR_{CUT}$ (hatched portion). Since all the points on the edge of the blade move along arcuate or circular loci of the same shape when the blade 31 is cutting the cornea, there arises no difference in cutting depending on the position of the blade, so that a satisfactory incised surface can be obtained. In addition, the portion $AR_{HIN}$ which is not incised is formed as the hinge on the upper side (upper eyelid side) of the patient's eye by virtue of the above-described positional arrangement of the links 46a and 46b. Since the holding portion of the apparatus body (the tube 12b side) is located laterally with respect to the patient's eye (at the ear side), the cheek and the like do not hinder the formation of the upper hinge flap.

The blade 31 subsequently continues to rotatively move, and when it reaches the position of $S_{CUT}$ (solid line) upon one rotation, the control unit 60 controls the drive motor 21 to stop the blade 31 at that position. The operator may operate the foot switch 62 through observation to stop the blade 31.

In the apparatus of this embodiment, the cutting unit 3 is arranged to be movable in the form in which it is suspended from the coupling unit 2, and a guide member and the like for moving the cutting unit 3 are not provided on the suction unit 1. Consequently, the apparatus is free from a trouble that the eyelashes of the patient's eye is nipped.

After the formation of the flap with the upper hinge remaining in the above-described manner, air is allowed to flow into the gap $AR_{SU}$ to cancel the suction, and the apparatus is removed from the patient's eye. Subsequently, the corneal stroma is ablated at a refractive correction amount by laser light, and the flap is then returned to its original position, thereby completing the surgery.

When the other eye (right eye) is to be operated, the transfer unit 4 is removed, and is replaced to the notched portion 20R side. This can adapt the apparatus to the surgical operation for the right eye in which the upper hinge flap is formed while holding the vacuum tube 12b side in such a way that it is located on the right ear side of the patient.

In the incision based on the movement of the blade 31 by making use of the above-described rotation of the links, the rotation of the links at a fixed speed results in the substantial difference in the moving speed of the blade 31 in the direction toward the hinge depending on the rotational position (angle of rotation), which may lead to different surface roughness of the incised surface. In this case, the rotating speed of the drive motor 21 can be controlled so as not to largely vary the moving speed of the blade 31 in the direction toward the hinge depending on the location by correlating the rotating position of the links and the moving speed of the blade 31 (the moving speed in the lateral direction and the moving speed toward the hinge).

In addition, since the apparatus of this embodiment is designed so that the units are separable, processing such as storage and cleaning can be effected easily.

Figure 6A:
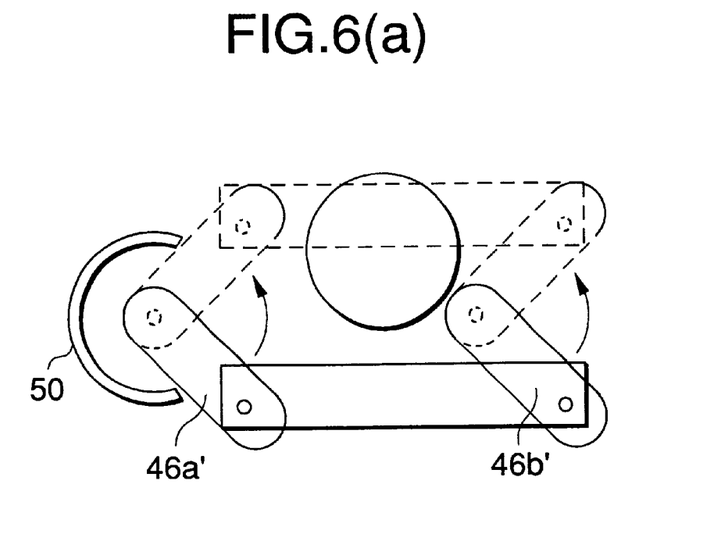
Figure 6B:
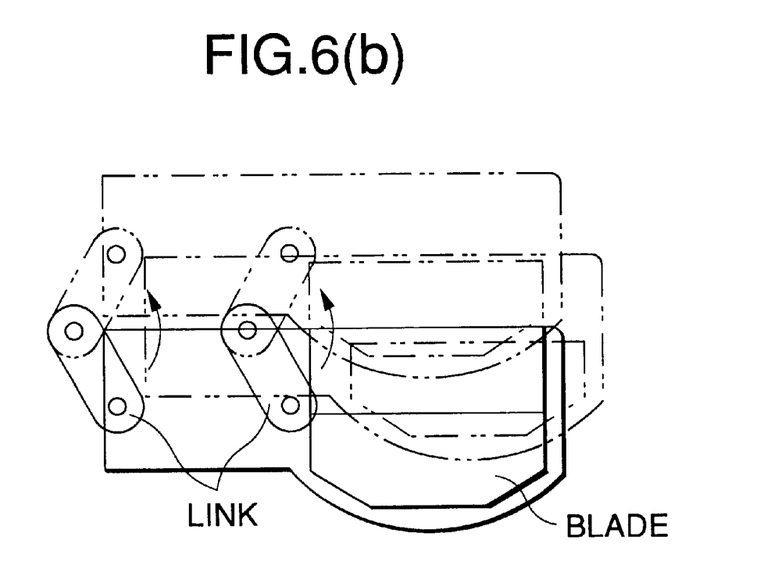

Although the above-described embodiment is arranged such that the cornea can be incised while securing the hinge as the two links undergo half rotation, links 46a' and 46b' may secure the hinge upon rotation of an angle which is smaller than the half rotation as shown in FIG. 6(a). In this case, the hinge can be secured by restricting the rotation of the links (or the movement of the blade itself) by providing a stopper 50 or by controlling the amount of rotation of the motor. In addition, although in the embodiment the blade is interposed between the two links, the blade may be disposed on the outer side, as shown in FIG. 6(b).

Furthermore, although in the embodiment the drive motor is used for the movement of the blade, a rotating knob or the like which rotates the links 46a and 46b in synchronism with each other may be provided, and may be rotated manually to move the blade.

Although the present invention has been described with reference to the embodiment, it goes without saying that a mechanism for laterally oscillating the blade may be added.

As described above, in accordance with the present invention, the cornea (particularly the Bowman's membrane at the cutting start) can be incised smoothly by ensuring the cutting ability of the blade in a simple arrangement.

The upper hinge flap can be formed easily through the parallel movement of the blade while the apparatus is positioned by being held from the side surface side of the patient's eye.

The feeding of the blade with respect to the hinge is parallel, and no difference is produced in the incision depending on the location of the edge of the blade. For this reason, it is possible to obtain a satisfactory incised surface by which the irregularities on the corneal surface at the time of adhesion can be reduced even if slight positioning error may occur at the time of placing the flap back in the original position.

Since the edge of the blade slidingly moves in the lateral direction in such a manner as to depict arcuate loci of the same shape, the angle of incision of the edge of the blade can be substantively reduced as compared to the blade which is adapted to move linearly or the blade which is adapted to pivot by using one axis as a reference, so that smooth incision can be effected.

Since the guide for feeding the blade is not provided on the suction portion, it is possible to prevent the problem of nipping the eyelashes of the patient's eye during the surgical operation.

What is claimed is:

1. A corneal surgical apparatus for incising a cornea of a patient's eye in a layered form, comprising:
fixing means, having an opening, for fixing a periphery of said cornea relative to said apparatus so that said cornea projects from said opening;
applanating means for applanating said cornea projecting from said opening;
a blade for incising said cornea applanated by said applanating means; and
moving means for moving said blade, wherein said moving means includes:
first and second links, each rotatably coupled to said blade, said first and second links being parallel to each other and equal in length to each other, and
rotating means for rotating rotational shafts of said first link and said second link in synchronism with each other.

2. A corneal surgical apparatus according to claim 1, wherein said blade is moved by said moving means without making an oscillating motion.

3. A corneal surgical apparatus according to claim 1, wherein positions of the rotational shafts of said first and said second links, and a position of an edge of said blade coupled to said first and said second links are determined in relation to a position of a center of said opening and a size of said opening, so that said opening provided in said fixing means partially remains outside of a movable range of said blade moved by said moving means.

4. A corneal surgical apparatus according to claim 1, further comprising:
restricting means for restricting movement of said blade to secure a hinge in the cornea incised by said blade.

5. A corneal surgical apparatus according to claim 1, further comprising:
suspending means for suspending and supporting said moving means, said applanating means, and said blade with respect to said fixing means.

6. A corneal surgical apparatus according to claim 1, wherein a direction of an edge of said blade is in parallel to a longitudinal direction of said fixing means.

7. A corneal surgical apparatus according to claim 1, wherein said moving means and said blade are bilaterally symmetrical, and said apparatus further comprising:
attaching means for attaching said moving means and said blade in an inverted form with respect to said fixing means.

8. A corneal surgical apparatus according to claim 1, further comprising:
driving means for driving said moving means; and
controlling means for controlling said driving means to vary a moving speed of said blade during incision.

9. A corneal surgical apparatus for use in photorefractive keratectomy, comprising:
a suction unit having a vacuum ring;
a coupling unit mounted on said suction unit;
a transfer unit mounted on said coupling unit and having a parallel link mechanism; and
a cutting unit including:
a base;
a cornea applanating portion fixedly provided on said base; and
a blade fixedly provided on said base,
wherein said base of said cutting unit is attached to said transfer unit by said parallel link mechanism.

10. A corneal surgical apparatus according to claim 9, wherein a relative positional relationship between said cornea applanating portion and said blade is kept constant by said base.

11. A corneal surgical apparatus according to claim 9, wherein said blade is in non-contact with said cornea applanating portion.

12. A microkeratome according to claim 9, wherein said parallel link mechanism moves said base so that a point on an edge of said blade moves along an arcuate locus of a same shape as an arcuate locus along which another point on said edge of said blade moves.

13. A corneal surgical apparatus according to claim 9, wherein said base of said cutting unit is rotationally mounted about a stationary point via said parallel link mechanism.

14. A corneal surgical apparatus according to claim 13, wherein said stationary point corresponds to a center of an opening of said suction unit.

15. A corneal surgical apparatus for use in photorefractive keratectomy, comprising:
a suction unit having a vacuum ring;
a coupling unit mounted on said suction unit;
a cutting unit having a blade;
a transfer unit mounted on said coupling unit and having a parallel link mechanism,
wherein said cutting unit is rotationally mounted about a stationary point via said parallel link mechanism.

16. A corneal surgical apparatus according to claim 15, wherein said stationary point corresponds to a center of an opening of said suction unit.

17. A parallel link mechanism of a corneal surgical apparatus, said parallel link mechanism comprising:
a base; and
a pair of links rotationally arranged with respect to said base about rotational axes, respectively, both of said links rotatably supporting a blade so that said links are kinematically connected to each other through the blade, wherein the blade rotates about an axis other than said rotational axes of said links, and wherein the parallel link mechanism is adapted to move the blade to incise a cornea of a patient's eye.

18. A parallel link mechanism according to claim 17, wherein any portions on the blade orbit along arcuate loci of a same shape via said links.

19. A parallel link mechanism according to claim 17, wherein the blade is kept in parallel via said link during orbiting motion of the blade.

20. A corneal surgical apparatus for incising a cornea of a patient's eye in a layered form, comprising:
a fixing mechanism, having an opening, which fixes a periphery of said cornea relative to said apparatus so that said cornea projects from said opening;
an applanating device for applanating said cornea projecting from said opening;
a blade for incising said cornea applanated by said applanating device; and
a moving mechanism for moving said blade, wherein said moving mechanism includes:
first and second links, each rotatably coupled to said blade, said first and second links being parallel to each other and equal in length to each other, and
a rotating mechanism for rotating rotational shafts of said first link and said second link in synchronism with each other.

21. A corneal surgical apparatus for incising a cornea of a patient's eye in a layered form, comprising:
fixing means, having an opening, for fixing a periphery of said cornea relative to said apparatus so that said cornea projects from said opening;
applanating means for applanating said cornea projecting from said opening;
a blade for incising said cornea applanated by said applanating means; and
moving means for moving said blade so that a point on an edge of said blade moves along an arcuate locus of a same shape as an arcuate locus along which another point on said edge of said blade moves;

wherein said blade is moved by said moving means without making an oscillating motion.

22. A corneal surgical apparatus for incising a cornea of a patient's eye in a layered form, comprising:

fixing means, having an opening, for fixing a periphery of said cornea relative to said apparatus so that said cornea projects from said opening;

applanating means for applanating said cornea projecting from said opening;

a blade for incising said cornea applanated by said applanating means; and moving means for moving said blade so that a point on an edge of said blade moves along an arcuate locus of a same shape as an arcuate locus along which another point on said edge of said blade moves, wherein said moving means includes:

first and second links, each rotatably coupled to said blade, said first and second links being parallel to each other and equal in length to each other; and rotating means for rotating rotational shafts of said first link and said second link in synchronism with each other.

\* \* \* \* \*